US00PP33977P2

(12) United States Plant Patent
Verhoef

(10) Patent No.: US PP33,977 P2
(45) Date of Patent: Mar. 1, 2022

(54) ***WEIGELA* PLANT NAMED 'JS4'**

(50) Latin Name: ***Weigela* hybrid**
Varietal Denomination: JS4

(71) Applicant: Gijsbertus Verhoef, Hazerswoude-Dorp (NL)

(72) Inventor: Gijsbertus Verhoef, Hazerswoude-Dorp (NL)

(73) Assignee: BERT VERHOEF BOOMK WEKERIJ B.V., Hazerswoude-Dorp (NL)

( * ) Notice: Subject to any disclaimer, the term of this patent is extended or adjusted under 35 U.S.C. 154(b) by 0 days.

(21) Appl. No.: 17/335,802

(22) Filed: Jun. 1, 2021

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Weigela* plant named 'JS4' that is characterized by its upright plant habit, its medium-sized plant, its leaves that are green in color, its flowers that are deep pink in color, and its continuous blooming period from spring into fall.

2 Drawing Sheets

Botanical classification: *Weigela* hybrid.
Variety denomination: 'JS4'.

CROSS REFERENCE TO A RELATED APPLICATION

This application is related to a European plant breeders' rights application filed on Mar. 23, 2020, application No. 2020/0837. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Weigela* of hybrid origin and will be referred to hereafter by its cultivar name, 'JS4'. 'JS4' represents a new cultivar of *Weigela*, a deciduous shrub grown for landscape use.

The new Invention arose from an ongoing controlled breeding program in Hazerswoude-Dorp, The Netherlands. The objective of the breeding program is to develop hybrid cultivars of *Weigela* with unique and superior garden attributes. In particular, to develop cultivars that are more compact, rich-flowering and remontant-flowering.

The Inventor made a controlled cross in June of 2015 in Hazerswoude-Dorp, The Netherlands between *Weigela* cultivars 'JS2' (not patented) as the female parent and 'Red Prince' as the male parent (not patented). 'JS4' was selected in June of 2018 as a single unique plant amongst the resulting seedlings.

Asexual propagation of the new cultivar was first accomplished by softwood stem cuttings by the Inventor in June of 2018 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'JS4' as a unique cultivar of *Weigela*.

1. 'JS4' exhibits an upright plant habit.
2. 'JS4' exhibits a medium-sized plant.
3. 'JS4' exhibits leaves that are green in color.
4. 'JS4' exhibits flowers that are deep pink in color.
5. 'JS4' exhibits a continuous blooming period from spring into fall.

The female parent of 'JS4' differs from 'JS4' in having a lower growing plant habit, an irregular plant shape, and flowers that are pale pink in color. The male parent of 'JS4' differs from 'JS4' in having flowers that are red in color and in not continuously blooming from spring into fall. 'JS4' can be most closely compared to the *Weigela* cultivars 'Carnaval' (not patented) and 'Abel Carrière' (not patented). 'Carnaval' is similar to 'JS4' in plant shape. 'Carnaval' differs from 'JS4' in having larger flowers that are lighter pink in color, and in not continuously bloom from spring into fall. 'Abel Carrière' is similar to 'JS4' in foliage color and shape. 'Abel Carrière' differs from 'JS4' in having flowers that are purple-pink in color, a more broadly spreading plant habit, and in blooming less continuously from spring into fall.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website or facebook postings by van vilet New Plants, allsummer and Bert Verhoef Boomkwekerij.

BRIEF DESCRIPTION OF THE DRAWINGS

The accompanying color photographs illustrates the overall appearance and distinct characteristics of the new *Weigela*. The photographs were taken of a three-year-old plant as grown outdoors in a trial field in Hazerswoude-Dorp, The Netherlands.

The photograph in FIG. 1 provides a side view of the plant habit of 'JS4' in bloom.

Figure 1:
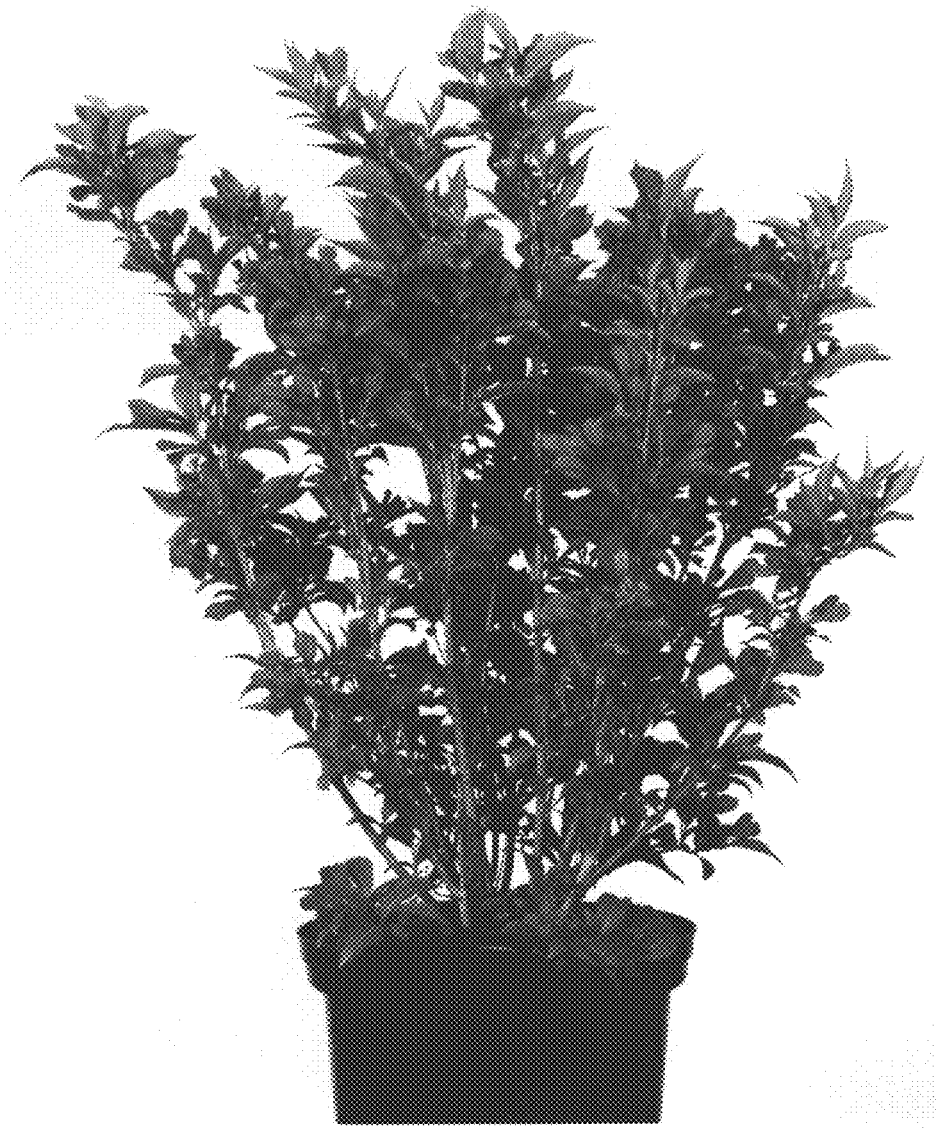
Figure 2:
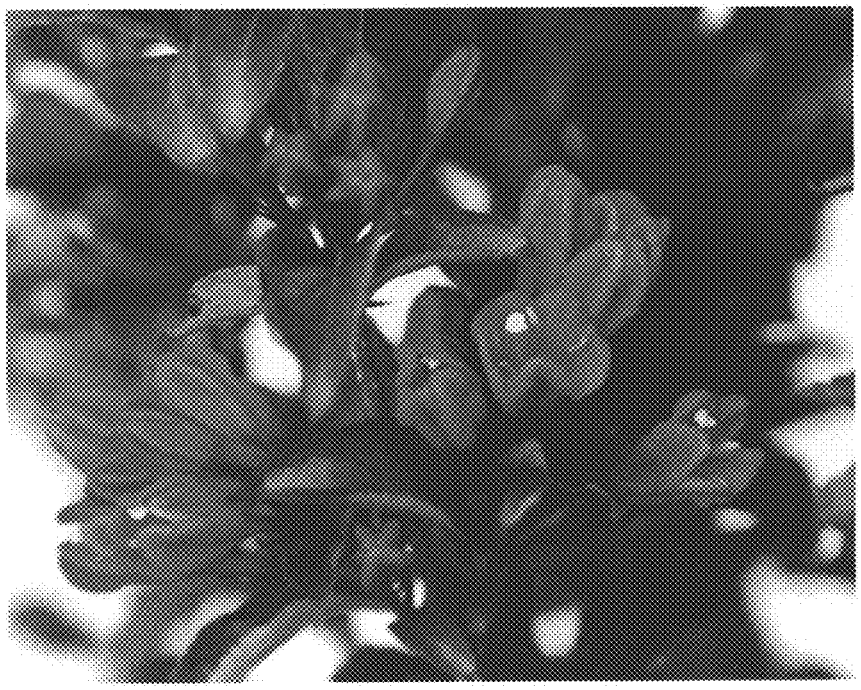

The photograph in FIG. 2 provides a close-up view of the flowers of 'JS4'.

Figure 3:
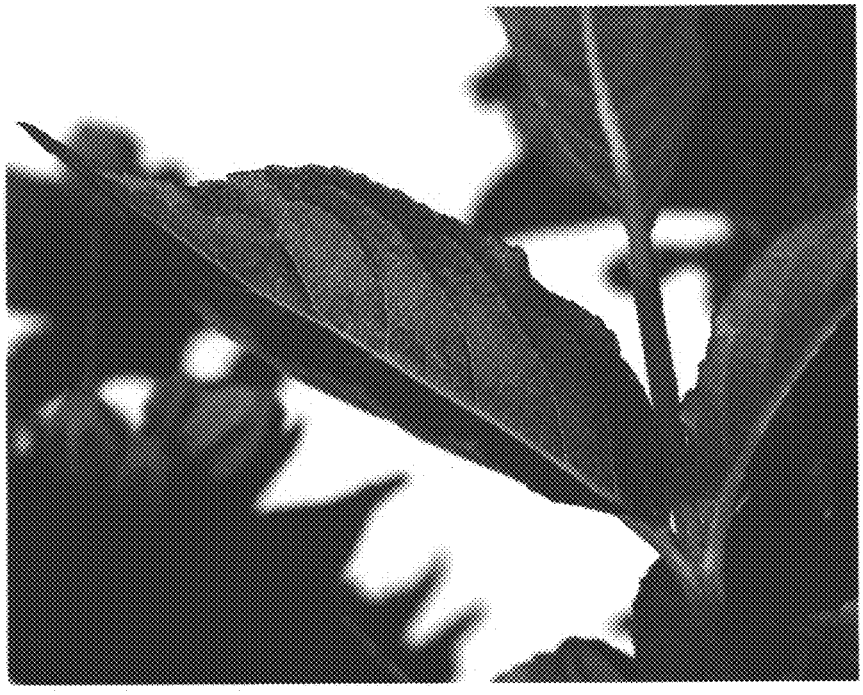

The photograph in FIG. 3 provides a close-up view of the foliage of 'JS4'.

The colors in the photographs may differ slightly from the color values cited in the detailed botanical description, which accurately describe the colors of the new *Weigela*.

DETAILED BOTANICAL DESCRIPTION

The following is a detailed description of three-year-old plants as grown outdoors in a trial field in Hazerswoude-Dorp, The Netherlands. Phenotypic differences may be observed with variations in environmental, climatic, and cultural conditions. The color determination is in accordance with The 2015 Colour Chart of The Royal Horticultural Society, London, England, except where general color terms of ordinary dictionary significance are used.

General description:

*Blooming period*.—Late spring in mid-May into fall in October in The Netherlands.

*Plant type*.—Deciduous shrub.

*Plant habit*.—Compact, upright.

*Plant size*.—An average of 67.3 cm in height (soil level to top of foliar plane), 65 cm in height (soil level to top of floral plane) and 63.5 cm in diameter as a 3-year old plant, reaches about 200 cm in height and 125 cm in width as a mature plant in the landscape.

*Hardiness*.—At least in U.S.D.A. Zones 5 to 9.

*Diseases and pests*.—No susceptibility to resistance to diseases or pests has been observed.

*Root description*.—Fibrous, moderately dense.

*Propagation*.—Softwood stem cuttings.

*Root initiation*.—An average of 6 weeks.

*Root development*.—An average of 3 months to produce a young rooted plant.

*Growth rate*.—Moderately vigorous.

Branch description:

*Branch shape*.—Slightly quadrangular.

*Branch color*.—Young; 146C, mature stems; N170A, old wood; 197C, 199B, and N200C, internodes N186C.

*Branch size*.—An average of 47.6 cm in length and 5 mm in diameter.

*Branch surface*.—Slightly glossy, angles of stems moderately to densely covered with short adpressed hairs average of 1 mm in length and is too small to measure color.

*Branch aspect*.—Upright to outward at an average angle of 40° from vertical.

*Branch quantity*.—Freely branched, an average of 13 main branches, 15 lateral branches per main branch.

*Branch strength*.—Moderately strong.

*Internode length*.—Average of 6 cm.

Foliage description:

*Leaf shape*.—Elliptic to obovate.

*Leaf division*.—Simple.

*Leaf base*.—Obtuse to very short attenuate.

*Leaf apex*.—Apiculate.

*Leaf fragrance*.—None.

*Leaf venation*.—Pinnate, color upper surface; 151C, lower surface 145C.

*Leaf margins*.—Serrate.

*Leaf arrangement*.—Opposite or in whorls of three.

*Leaf attachment*.—Petiolate.

*Leaf surface*.—Upper surface slightly glossy, lower surface matte, both surfaces are smooth and glabrous, slightly rugose, upper and lower surface main vein moderately covered with very short hairs, an average of 0.5 mm in length and too small to measure color.

*Leaf size*.—An average of 6.7 cm in length and 3.4 cm in width.

*Leaf quantity*.—An average of 6 (3 pairs) per lateral branch.

*Leaf color*.—Young upper surface; 144A, narrowly margined 172A to 172B, young lower surface; 146C, narrowly margined 171B, mature upper surface; 143A, half narrowly margined 173A, mature lower surface; 146B, narrowly margined 171A.

*Petioles*.—Average of 5 mm in length, 4 mm in width, flattened, upper and lower surface color 144C, both surfaces matte and margins moderately pubescent with soft hairs and average of 1 mm in length and too small to measure color.

*Stipules*.—None.

Inflorescence description:

*Inflorescence type*.—Terminal raceme.

*Inflorescence size*.—5.3 cm in height (including peduncle), 5.2 cm in diameter.

*Flower buds*.—Narrow obovate to oblanceolate in shape, an average of 2.2 cm in length and 7 mm in diameter, 187D, surface is slightly glossy, smooth and sparsely covered with very short hairs, average of 0.2 mm in length, too small to measure color.

*Flower fragrance*.—None.

*Lastingness of flowers*.—About 12 days, self-cleaning.

*Flower aspect*.—Outward to slightly upright.

*Flower quantity*.—An average 6 per inflorescence, 750 flowers per plant.

*Flower type*.—Narrow campanulate, single.

*Flower size*.—Average of 1.8 cm in height and diameter, 3.6 cm in depth, throat; 9 mm in diameter, tube; 2.5 cm in length, 9 mm in diameter.

*Peduncles*.—Average of 9 mm in length and 1.75 mm in diameter, held in a vertical angle to lateral branch, strong, 144A to 144B in color, matte and sparsely pubescent covered with soft hairs an average of 1 mm in length and too small to measure color.

*Pedicels*.—Average of 4 mm in length and 1 mm in diameter, held in an angle of 20° to lateral branch, strong, 143B in color, slightly glossy.

*Calyx.*—Rotate in shape, an average of 1.2 cm in length, 7 mm in diameter.

*Sepals.*—5, rotate, linear in shape, narrowly acute apex, cuneate base fused, entire margin, an average of 1.1 cm in length and 1 mm in width, upper and lower surface is smooth and glabrous, color; when opening upper surface 183A to 183B, fading at the base to 145B to 145C, when opening lower surface 183A, tinged 150C, when fully open 145C, margins 184A, upper half slightly tinged 184A, when fully open lower surface 183A, tinged 150C.

*Petals.*—5, whorled, lower 70% fused into tube, spathulate in shape, margin entire on free portion, apex obtuse, an average of 3.6 cm in length, 9 mm in width, upper and lower surface glabrous, slightly velvety, color; when opening upper surface 60C, when opening lower surface 59C, when fully open upper surface 59D, fully open 59C, throat color 59D, tube; inner surface 59D, tinged 53B, outer surface broad portion 60C, narrow lower portion 53A.

Reproductive organs:

*Gynoecium.*—Pistil; 1, average of 3.5 cm in length, style; average of 3.3 cm in length, 145C, stigma; club-shaped, 2 mm in length, 2.5 mm in diameter, 145C in color, ovary; 143C in color.

*Androecium.*—Stamens; 5, filaments; a blend of 185C, 186C and 186D, average of 7 mm in length, anthers; 54C in color, an average of 5 mm in length, 0.75 mm in width, narrowly oblong in shape, pollen; moderate to high in quantity and 160C in color.

*Fruit and seed.*—No fruit or seed production has been observed to date.

It is claimed:

1. A new and distinct cultivar of *Weigela* plant named 'JS4' as herein illustrated and described.

* * * * *